(12) United States Patent
Xie et al.

(10) Patent No.: US 8,519,121 B2
(45) Date of Patent: Aug. 27, 2013

(54) DEXTRAN FOR TREATING LUNG CANCER

(75) Inventors: Jinkui Xie, Guangzhou (CN); Anqiang Zhang, Guangzhou (CN); Jianguo Cao, Guangzhou (CN)

(73) Assignee: Guangzhou Konzern Pharmaceutical Co., Ltd., Guangzhou (CN)

( * ) Notice: Subject to any disclaimer, the term of this patent is extended or adjusted under 35 U.S.C. 154(b) by 3 days.

(21) Appl. No.: 13/000,194

(22) PCT Filed: Jun. 23, 2008

(86) PCT No.: PCT/CN2008/071414
§ 371 (c)(1),
(2), (4) Date: Jul. 13, 2011

(87) PCT Pub. No.: WO2009/155742
PCT Pub. Date: Dec. 30, 2009

(65) Prior Publication Data
US 2011/0263842 A1  Oct. 27, 2011

(51) Int. Cl.
*C08B 37/02* (2006.01)
(52) U.S. Cl.
USPC .......................................................... 536/112

(58) Field of Classification Search
USPC .......................................................... 536/112
See application file for complete search history.

(56) References Cited

U.S. PATENT DOCUMENTS
6,307,013 B1 * 10/2001 Chivers .......................... 530/311

FOREIGN PATENT DOCUMENTS
| CN | 1546531 A | 11/2004 |
| CN | 1939346 A | 4/2007 |
| WO | WO 2007/124625 | * 11/2007 |

OTHER PUBLICATIONS

Ricketts CR. Chemistry of dextran and its derivatives. Proc R Soc Med 44:558-559, Jul. 1951.*
Wei Chuanwan et al., Guang Dong, Hua Gong, Research Advancement of Polysaccharides, vol. 1, 2004, P36-40, 11, ISSN: 1007-1865.
International Search Report (Mailing Date Apr. 2, 2009) for PCT/CN2008/071414, Filed on Jun. 23, 2008.

* cited by examiner

*Primary Examiner* — Wu-Cheng Winston Shen
*Assistant Examiner* — Yih-Horng Shiao
(74) *Attorney, Agent, or Firm* — Vic Y. Lin; Joseph G. Chu; Innovation Capital Law Group, LLP

(57) ABSTRACT

Dextran for preparing medicine for anti-lung cancer, has repeated structure unit and molecular weight of 1.5-2.5 million Daltons. The dextran is extracted from land slug.

1 Claim, 19 Drawing Sheets

DEXTRAN FOR TREATING LUNG CANCER

TECHNOLOGY FIELD

The present invention relates to a dextrose polymer, particularly relates to a dextran which is used for anti-cancer.

BACKGROUND ART

In existing art, Lung cancer, a kind of malignant cancers, has become the first killer to human's health. Incidence of lung cancer increases at 11.90% in recently 10 years due to the aggravating environmental pollution. Up to 2000, there are more than 10,000,000 cases of malignant cancers in the world, in which there are 1,239,000 cases of lung cancer. Up to 2000, there are about 6,200,000 persons died by malignant cancers, in which there are 1,103,000 persons died by lung cancer. The lung cancer has become first deadly malignant cancer. Now there are 1,500,000 to 1,800,000 persons died by lung cancer each year in the world. In China, the rate is 83.43 persons per 100,000 persons. There are more than 1,000,000 cases each year in China, and there are more than 600,000 persons died by lung cancer. Therefore, how to find the effective new drug for anti-lung cancer has become the hot problem in the medical field.

The current methods and related drugs for treatment of the lung cancer, surgical resection, radiation therapy, and chemotherapy, have some limitation. Once the patient is clinically diagnosed with lung cancer, 80% patients will lost the chance of surgical resection. Radiation therapy will bring damage to normal tissues, and this therapy method cannot be used in widely range. Chemotherapy will bring general cytotoxicity with high dose. The drug therapy will bring some side effects to liver, kidney, bone marrow and digestive system so that the treatment effect is lower. Intervention therapy is difficult to deal with the continuously disseminated metastases of cancer cells. Molecular targeting (gene) therapy still has many problems need to be solved, for example, vector construction, linkage of vector and projectile, the distributing in human body, and changes in the metabolic process, etc.

Through prior research, inventors of the present invention find that a glycoprotein marked PE-40 which extracted from limax has direct inhibitory effect to the small cell lung cancer, and chemotherapy drug such as DDP and 5-FU, and cytokines such as TNF-α will enhance the inhibitory effect to the small cell lung cancer, and these drugs have no toxicity and side effects. Though glycoprotein PE-40 is better than the other drugs, the glycoprotein is easy to sensitized and unstable due to the protein composition, which limits its apply range. The object of the present invention is to remove the protein and retain the polysaccharide of the glycoprotein PE-40, and try to keep the inhibitory effect. The dextran of the present invention could interfere with the normal metabolism of DNA and RNA of cancer cells, and promote the death of cancer cells, and inhibit the foci of the cancer.

The present invention further provides the polysaccharide composition KY-1 of the above polysaccharide mixture original from glycoprotein PE-40, and determinates the molecular structure of a sub-composition KY-1-1 of the polysaccharide KY-1.

CONTENTS OF THE INVENTION

The invention provides a dextran with molecular weight of 1.5-2.5 million Daltons, said dextran comprising the following repeated structure unit:

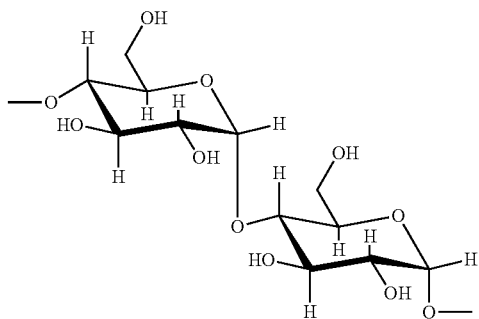

The dextran of the invention is extracted from limax (*Agriolimax agreslis* Linnaeus).

Through prior research, inventors of the present invention find that a glycoprotein marked PE-40 which extracted from limax has direct inhibitory effect to the small cell lung cancer, and chemotherapy drug such as DDP and 5-FU, and cytokines such as TNF-α will enhance the inhibitory effect to the small cell lung cancer, and these drugs have no toxicity and side effects. Though glycoprotein PE-40 is better than the other drugs, the glycoprotein is easy to sensitized and unstable due to the protein composition, which limits its apply range. The object of the present invention is to remove the protein and retain the polysaccharide composition of the glycoprotein PE-40, and try to keep the inhibitory effect. The dextran of the present invention could interfere with the normal metabolism of DNA and RNA of cancer cells, and promote the death of cancer cells, and inhibit the foci of the cancer. The present invention further provides the polysaccharide compositions KY-1, KY-2 and KY-3 of the above polysaccharide mixture original from glycoprotein PE-40, and then separates the sub-composition KY-1-1 and KY-1-2 from the polysaccharide KY-1. We find that the sub-composition KY-1-1 is the best composition, and then determinate the molecular structure of KY-1-1 as a dextran.

The invention further provides a use of the above dextran (KY-1-1) in preparation of pharmaceutical compositions for treatment of lung cancer. The pharmaceutical composition comprises of effective amount of the dextran according to the present invention, and pharmaceutically acceptable excipients, thinners, and carriers. The pharmaceutical composition is in the form of: capsule, granulate, tablet, pill, guttate pill, injection, and frozen powder for injection.

The dextran KY-1-1 according to the present invention is prepared by the following method: first, extract the crude polysaccharide from the glycoprotein; second, separate and purify the composition of the crude polysaccharide. The crude polysaccharide is prepared by adding ethanol for precipitating, and then removing protein by TCA, and the polysaccharide was obtained by dialyzing. The detailed process will be described in the embodiments below.

The dextran, according to the present invention, is a homogeneous polysaccharide of the crude polysaccharide from limax, and is found to be one of the best compositions which have best anti-cancer activity. The present invention lays the foundation of the further research for the synthesis of the dextran and the pharmacological effect of the dextran.

The principles and operation of preparation, molecular structure and pharmacodynamics of the dextran according to the present invention may be better understood with reference to the drawings and the accompanying embodiments. Accordingly, it is intended to embrace all such alternatives, modifications and variations that fall within the spirit and broad scope of the appended claims.

BRIEF DESCRIPTION OF THE DRAWINGS

The invention is herein described, by way of example only, with reference to the accompanying drawings, wherein.

DETAILED DESCRIPTION OF THE INVENTION

The dextran, according to the present invention, is extracted from Limax (*Agriolimax agrestis* Linnaeus). It is proved by experiments that the dextran has a best anti-lung cancer activity. It may be better understood with reference to the detailed description below.

I. Preparation of the Dextran from Limax Material

1. Extraction of the Crude Polysaccharide

Source of material: entire limax (*Vaginnins alte* Ferussac, 1821) Guangxi, China.

Weight flesh limax material 1604 g, and add water 1000 ml, whisk them by a homo-genizer, then concentrate the mixture by a centrifugal in 6000 r/min for 15 minutes in order to separate the supernatant and residue. Add water into the resulting residue and repeat the above steps, and then collect and combine each supernatant, concentrate into 1000 ml liquid. Add ethanol into the combined supernatant, adjust the final concentration to 60%, and settle it down overnight, then get the deposit by a centrifugal, and then obtain the crude extraction by freeze drying procedure. The crude extraction is 40 g, its yield ratio is 2.5%, and the content percent of polysaccharide is 16.9%.

Add water into the above crude extraction to dissolve the extraction, add 30% TCA under volume ratio 1:10, mix the solution for 15 min, settle it down for 30 min, then get the supernatant by a centrifugal, dialyze the supernatant by flowing water through membrane whose molecular weight cut-off is 10,000 Dalton. Finally obtain the crude polysaccharide by concentration and freeze drying procedure. The crude polysaccharide is 24 g, its yield ratio is 1.5%, and the content percent of polysaccharide is 19.8%. The effect of the crude polysaccharide is screened to find the most effective composition.

2. Separation and Purify of the Crude Polysaccharide

Dissolve the crude polysaccharide in room temperature, and remove the deposit by a centrifugal in 12000 r/min for 10 min. Dialyze the supernatant in a bag whose molecular weight cut-off is 1,000 Dalton in order to remove the TCA. Place the retain liquid on the ion exchange column, and then wash and collect the liquid-phase composition by the distilled water. Two compositions, named KY-1 and KY-2, are obtained by concentration and gel column chromatography S-100 procedure. And two sub-compositions, named KY-1-1 and KY-1-2, are obtained by continue separation through gel column chromatography S-400 procedure. The sub-composition KY-1-1 is the dextran according to the present invention.

II. Construction Determination of the Dextran from the Limax Extraction

Figure 1:
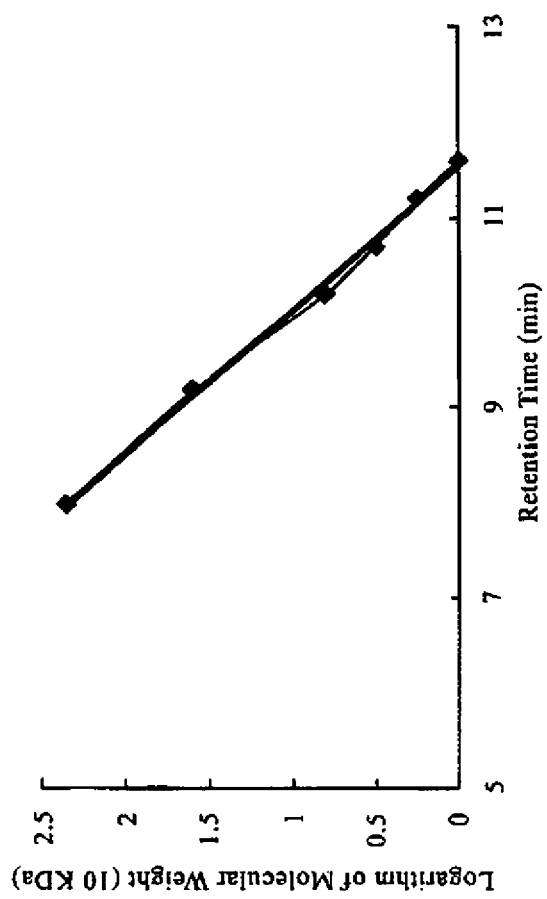
FIG. 1 is the view of the standard curve of a function of the molecular weight of the dextran to the retention time.

1. Detection of Purity and Molecular Weight of the Dextran (1) Standard Curve of the Dextran Weight Dextran T-2000, Dextran T-500, Dextran T-70, Dextran T-40 and Dextran T-10 0.01 g each, and dissolve them in 5 ml deionized water. Detect the retention time by HPLC, SHODEX SB-804 gel column, 200 nm. Draw the standard curve of the dextran with the retention time as x-coordinate and the logarithm of molecular weight of the dextran as y-coordinate, see FIG. 1, and then get the regression equation from the curve:

$$y=-0.6647x+7.6644$$

$$R^2=0.9961$$

Figure 2:
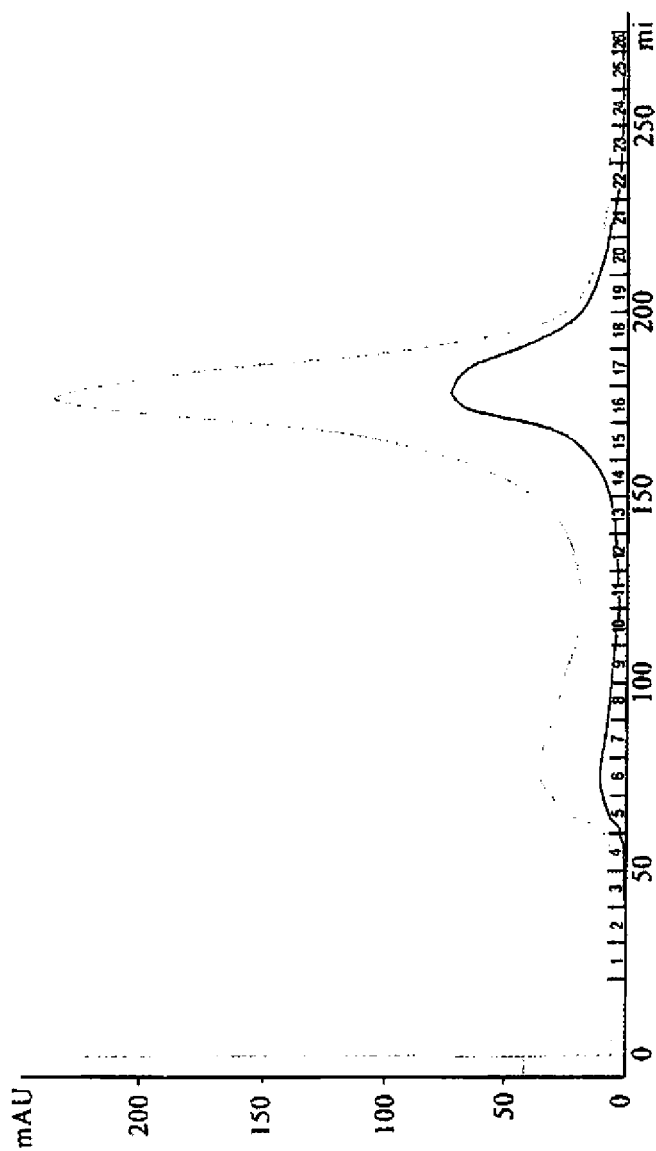
FIG. 2 is the HPLC map of two compositions separated from liquid-phase composition through gel chromatography system S-1000.
Figure 3:
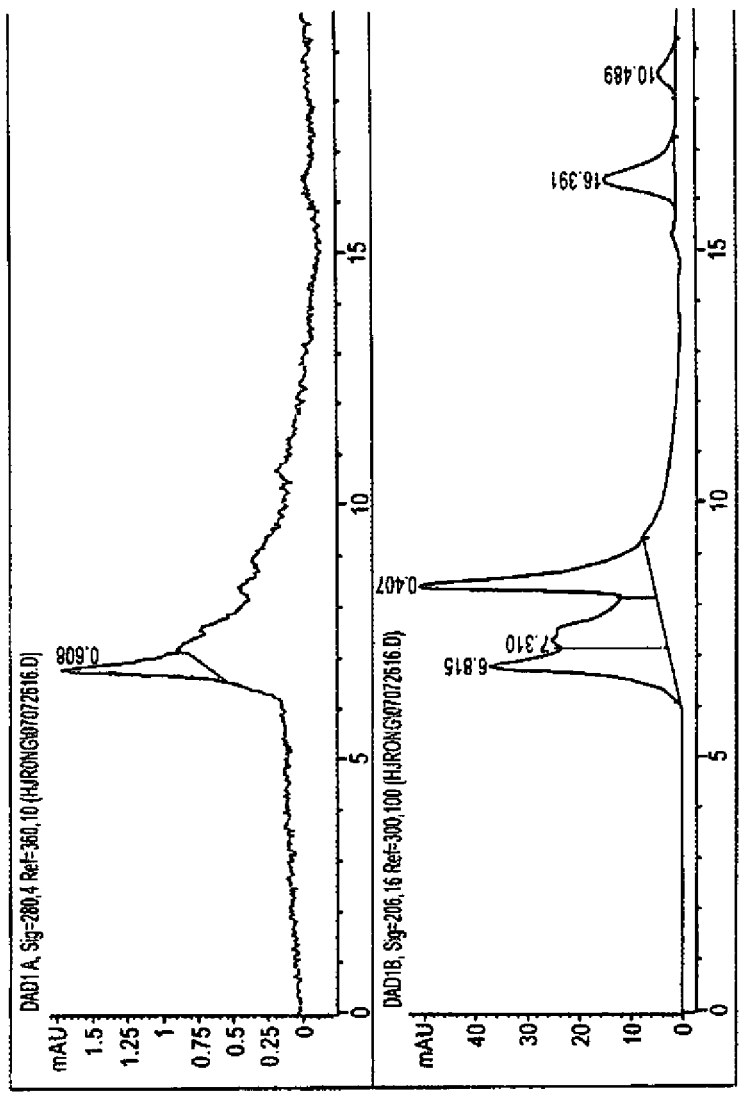
FIG. 3 is the HPLC map of two compositions separated from the composition KY-1 through gel chromatography system S-400.
Figure 4:
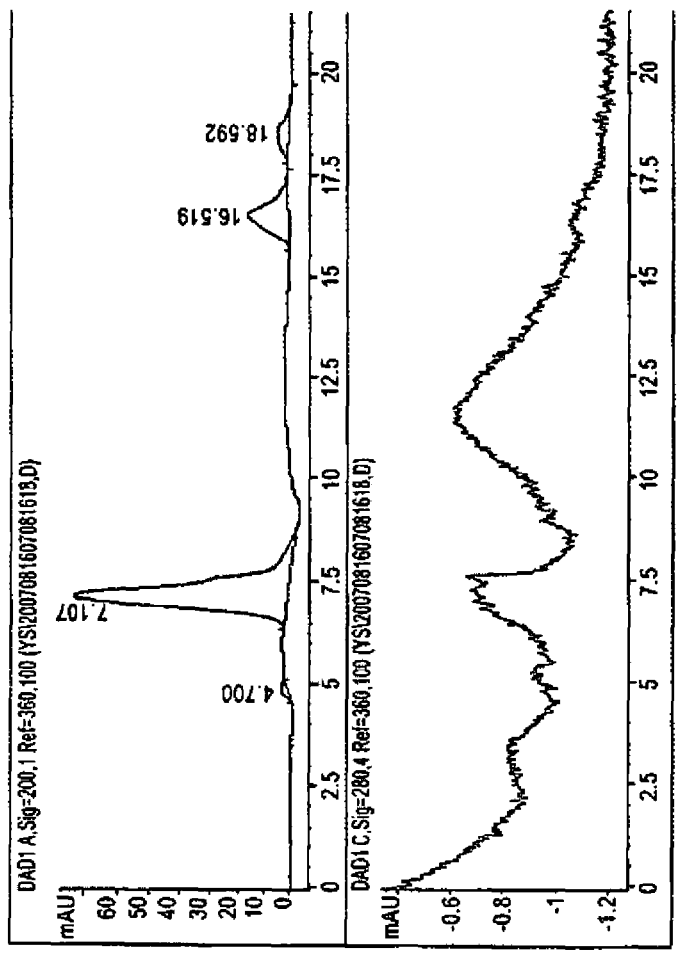
FIG. 4 is the HPLC map of the composition KY-1-1.
Figure 5:
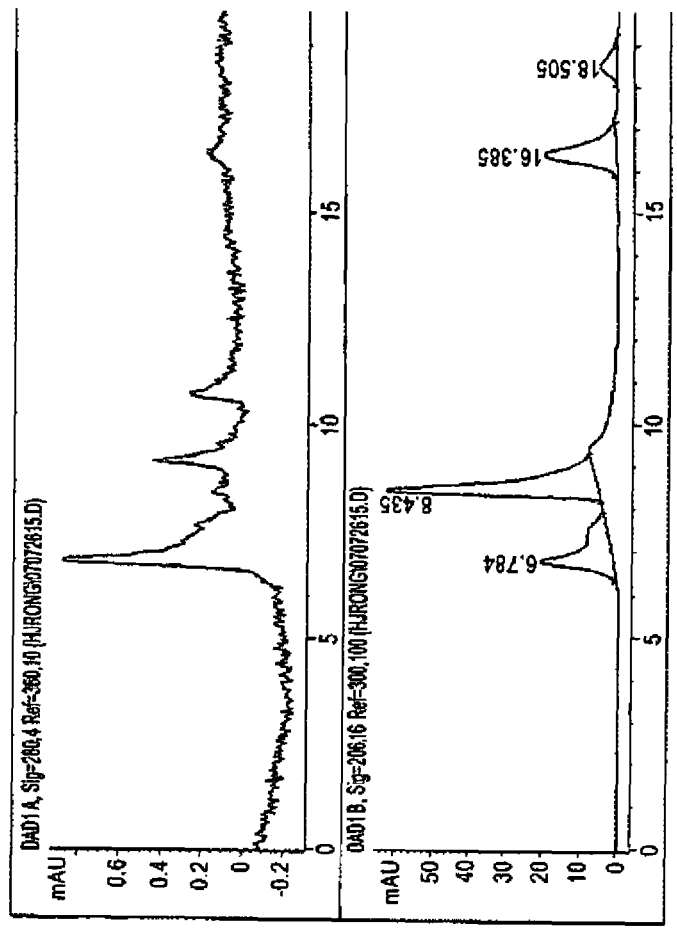
FIG. 5 is the HPLC map of the composition KY-1-2.
Figure 6:
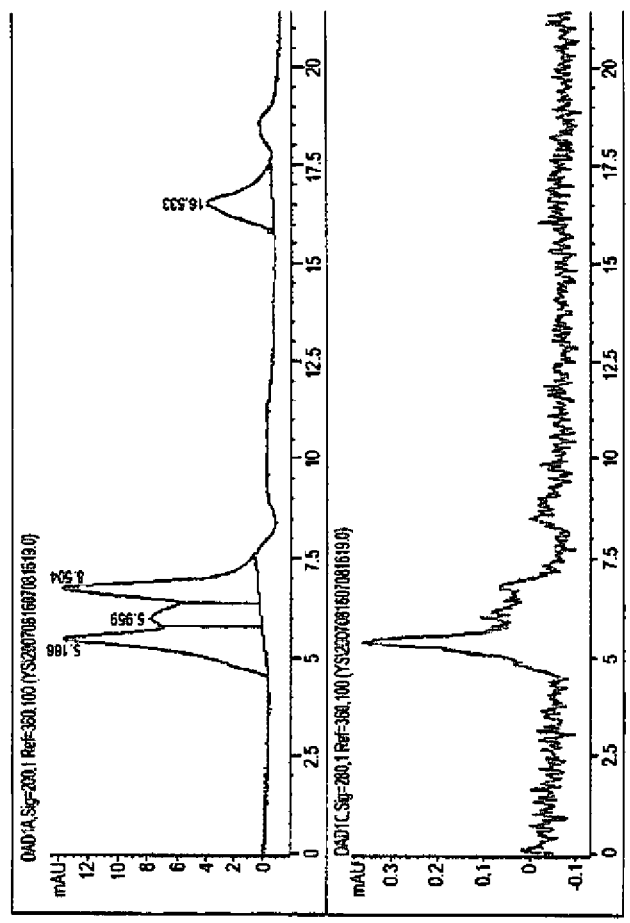
FIG. 6 is the HPLC map of the composition KY-2.

Operating parameters of HPLC is following:
One injection volume: 20 μl
Flowing phase: double distilled water
Velocity of flow: 0.8 ml/min
Temperature of the column: 40° C.
Detector: UV detector in 206 nm and 280 nm (2) HPLC Detecting Compositions KY-1, KY-1-1, KY-1-2 and KY-2 are analyzed by HPLC with the same operating parameters, see the results in FIG. 2-6. In FIG. 2, tubes 4-6 contains KY-1, and tubes 13-16 contains KY-2, red 190 nm, and blue 280 nm. Referring to the figures, it is found that the composition KY-1 has high purity and low absorption in 280 nm, and its molecular weight is more than 2,000,000 Dalton. It is also found that the composition KY-2 comprises at least three sub-compositions. The first sub-composition has certain absorption in 280 nm, and is proved as a homogeneous composition which is named KY-1-1. The other two sub-compositions are all mixture.

2. Detecting of the Content of the Polysaccharide (1) Drawing of the Standard Curve Weight 0.5000 g anhydrous glucose, analytical reagent, 105° C. dry, and dissolve it in 100 ml water, and take out 1 ml into a 50 ml flask, and add distilled water to 50 ml. Take 0.2 ml, 0.4 ml, 0.6 ml, 0.8 ml, 1.0 ml and 1.2 ml sample out of the flask into test tubes, three tubes for each sample, and then add distilled water to 2 ml, and add 5% phenol 1 ml, and then add concentrated sulfuric acid 5 ml, shake and heat it in boiling water for 15 min, and then cool it down in the ice-cold water, and then detect the absorbency in 490 nm by UV detector.

(2) Detecting the Dextran Sample

Take two sample, KY-1 and KY-2, to dissolve them into 1 mg/ml solution, and dilute it into 20, 40, 60 and 80 μg/ml. Mix 1 ml solution and 1 ml phenol in a 15 ml test tube by magnetic shaker, and add 5 ml concentrated sulfuric acid, shake and heat it in boiling water for 15 min, and then cool it down in the ice-cold water, and then detect the absorbency in 490 nm by UV detector.

$$\text{Polysaccharide (\%)} = \frac{\text{Weight of detected product (μg)}}{\text{Weight of original sample (μg)}} \times 100\%$$

See the result in table I. From table I, the content of polysaccharide of KY-1 is more than 90%.

TABLE I content of polysaccharide of each composition

| Composition | Absorbency | | | Crude polysaccharide (μg/ml) | Polysaccharide (%) |
|---|---|---|---|---|---|
| KY-1 | 0.490 | 0.622 | 0.525 | 60 | 90.1 |
| KY-2 | 0.275 | 0.303 | 0.303 | 60 | 32.3 |

3. UV Analysis of KY-1-1

Figure 7:
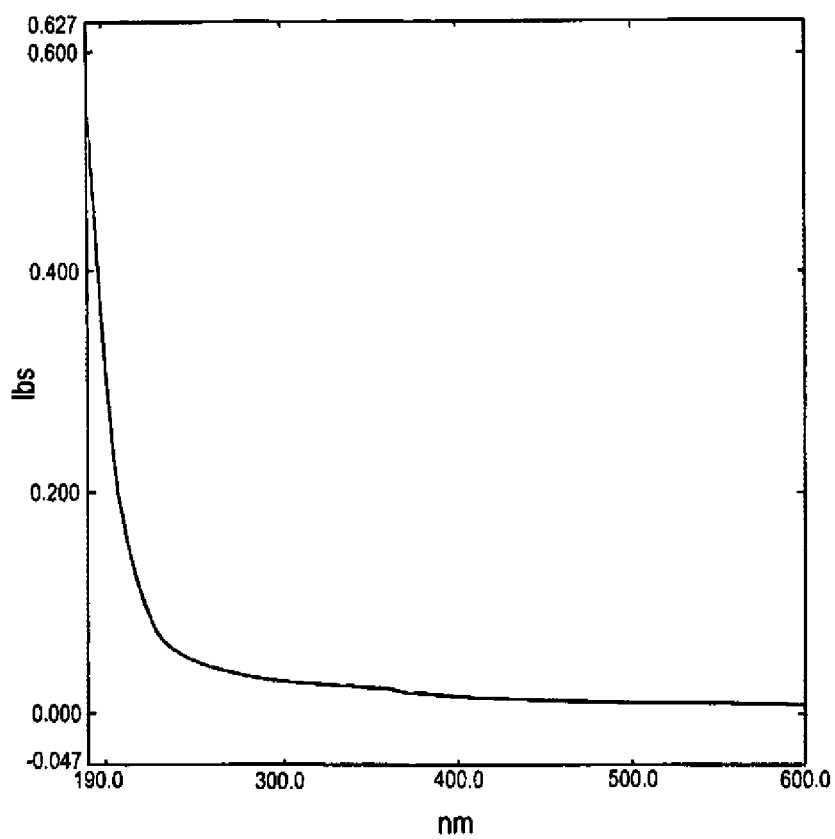
FIG. 7 is the full view of the UV scanning.

Weight sample 3 mg, dissolve it in distilled water to 1 mg/ml solution, full UV scan in 190600 nm. See result in FIG. 7, there is no absorbing peak in 280 nm and 260 nm, which means the dextran sample contains no protein and nucleic acid.

4. Analysis of the Composition of KY-1-1

(1) Acetylation of the Standard Sample of Monosaccharide

Figure 8:
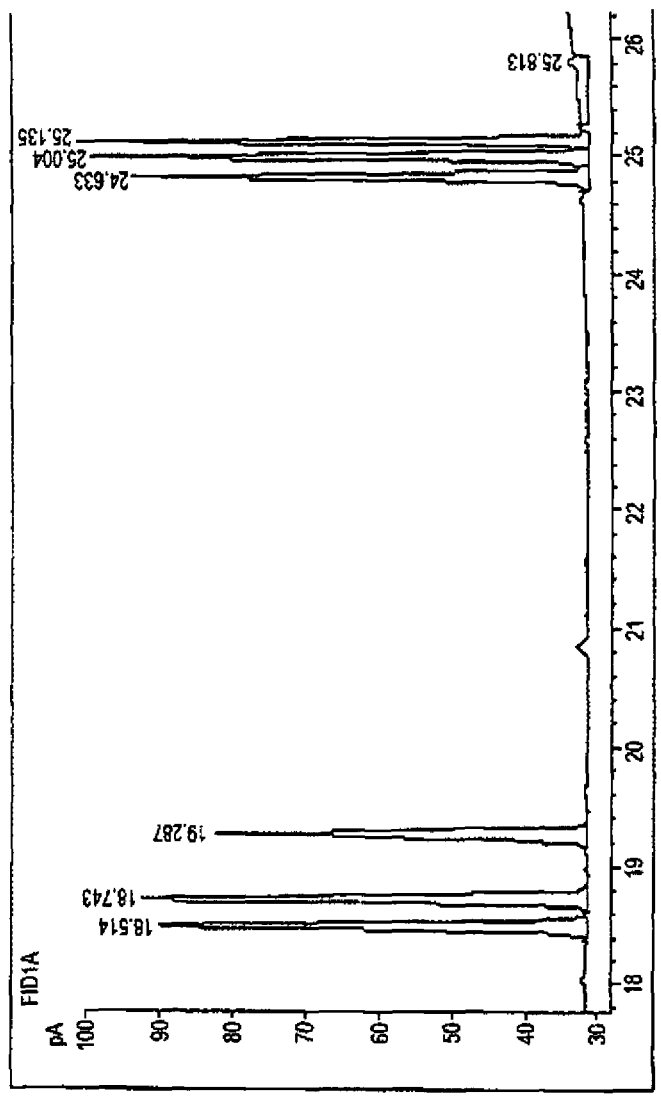
FIG. 8 is the gas chromatography map of the monosaccharide of the standard sample of the dextran.

Weight 2 mmol/L galactose, gucose, xylose, rhamnose, glucose, mannose and arabinose, and dissolve them in 3 ml distilled water separately. Add 20~30 mg $NaBH_4$, shake in room temperature for 3 hours, and then adjust the solution to pH 4-5 with acetic acid, then add 3 ml methanol, evaporated to dryness, repeat 4-5 times to remove the outgrowth boracic acid and water, and then place in a vacuum evaporator overnight. Heat in 110° C. for 15 minutes, remove the residual water, and then add 4 ml acetic anhydride in 100° C. for 1 hour, then cool it down, and add 3 ml toluene, evaporated to dryness, repeat 4-5 times to remove acetic anhydride. Dissolve the acetylated product by 3 ml chloroform, and separate the upper water solution and lower chloroform solution in a separatory funnel, remove the upper aqueous phase, repeat 4 times, collect the chloroform solution and dried by water-free sodium sulfate, then dissolve to 10 ml solution, and then make gas chromatography (GC) detection. Referring to FIG. 8, the result shows that six standard samples of above monosaccharide have been separated.

(2) Acetylation of Sample

Figure 9:
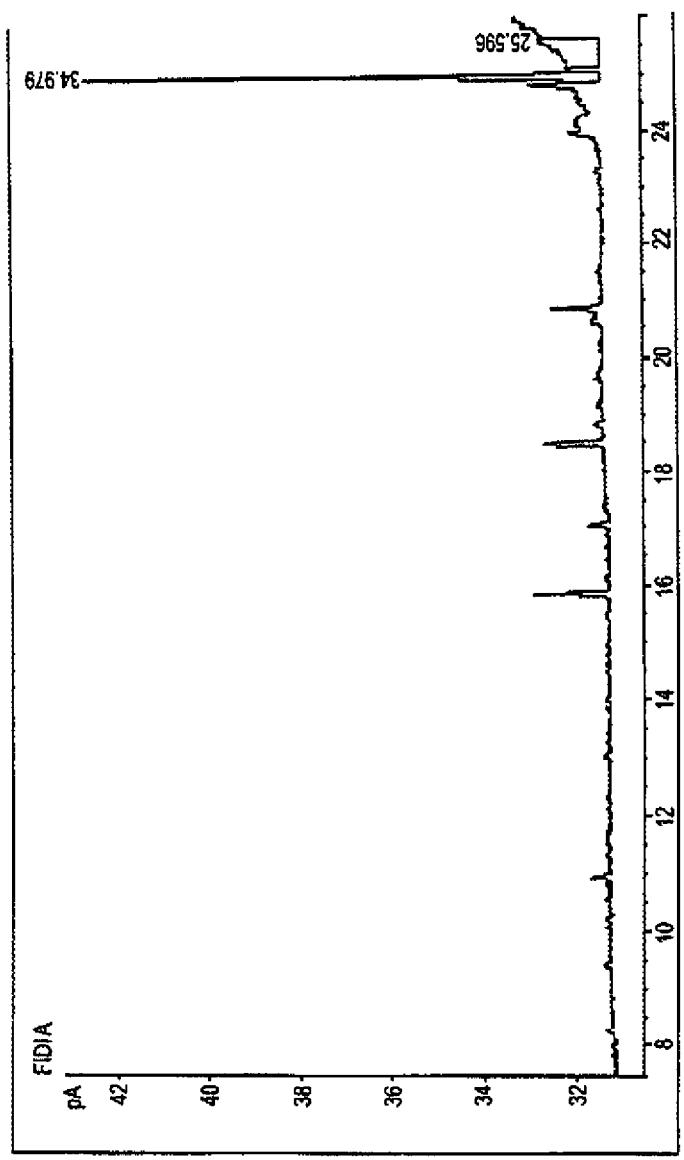
FIG. 9 is the gas chromatography map of the composition KY-1-1.

Take 2 mg KY-1-1 sample into a long test tube, add 2 mol/L TFA 4 ml, hydrolyzing in 110° C. for 2 hours. Evaporated to dryness in below 40° C., and then add 3 ml methanol, braise to remove the methanol, repeat 4-5 times to remove TFA. Proceed with the same procedure mentioned above, then dissolve to 10 ml solution, and then make gas chromatography (GC) detection. Referring to FIG. 9, the result shows that the KY-1-1 sample comprises glucose monosaccharide.

(3) Apparatus and Test Condition

Gas chromatography apparatus, equipped with quartz capillary column DB-23, 30 m×0.25 mm×0.25 μm. Flame Ionization Detector (FID), high purity nitrogen as carrier gas. Programmed temperature: initial temperature 120° C., raise to 240° C. in 15° C./min, constant temperature for 6.4 min. Injection port temperature 250° C., and diversion ratio 1:50. Detector temperature 250° C., hydrogen 35 ml/min, air 350 ml/min, makeup flow 30 ml/min. The flow velocity is 1 ml/min.

5. Analysis of Methylation of KY-1-1

(1) Preparation of NaOH-DMSO (0.025 g/ml)

Take 0.5 g NaOH and dissolve in 1 ml double distilled water, and then take 0.2 ml NaOH (50%) mix with 0.2 ml methanol, then dilute with 6 ml DMSO, and shake the NaOH-DMSO mixture by a mixer, and then ultrasonic treatment 3~5 min, collect NaOH deposit by a centrifugal. Repeat above three times, collect the NaOH deposit, and dissolve in 4 ml water.

(2) Steps of Methylation

Take sample of KY-1 12 mg into a test tube with lip, add 0.5 ml DMSO, ultrasonic treatment 2 min, and place in room temperature for 30 min, and then add 0.6 ml NaOH-DMSO mixture and 0.6 ml methylene iodide, close the lip, and ultrasonic treated and mixed for 7 minutes. Add 4 ml water to the mixture to stop the methylation. The methylated product is extracted by the same volume chloroform. Remove the upper aqueous phase, and collect the lower organic phase, and extract it by the same volume water five times. Concentrate the organic phase in 40° C. Repeat above procedure with DMSO 0.2 ml, NaOH-DMSO 0.2 ml, methylene iodide 0.3 ml, and water ml. Make a IR dectaction.

Dissolve the absolute methylated sample into 3 ml 88% formic acid, close the lip, 100° C. for 3 hours. Add methanol into rector bottle, evaporated to dryness in 40° C. Repeat above 3 times. Add 2 mol/L TFA 4 ml in 100° C. for 6 hours, and then evaporated to dryness in 40° C. Repeat above 5 times.

Dissolve the acid hydrolysed sample in 3 ml distilled water, and add 20 mg $NaSH_4$, close the lip, place in room temperature for 3 hours. Adjust to pH 4-5 with acetic acid, and add 3 ml methanol, evaporated to dryness. Repeat above 4-5 times. Vacuum dry it with $P_2O_5$ in room temperature overnight. Then heat it in 100° C. oven for 15 minutes.

Figure 10:
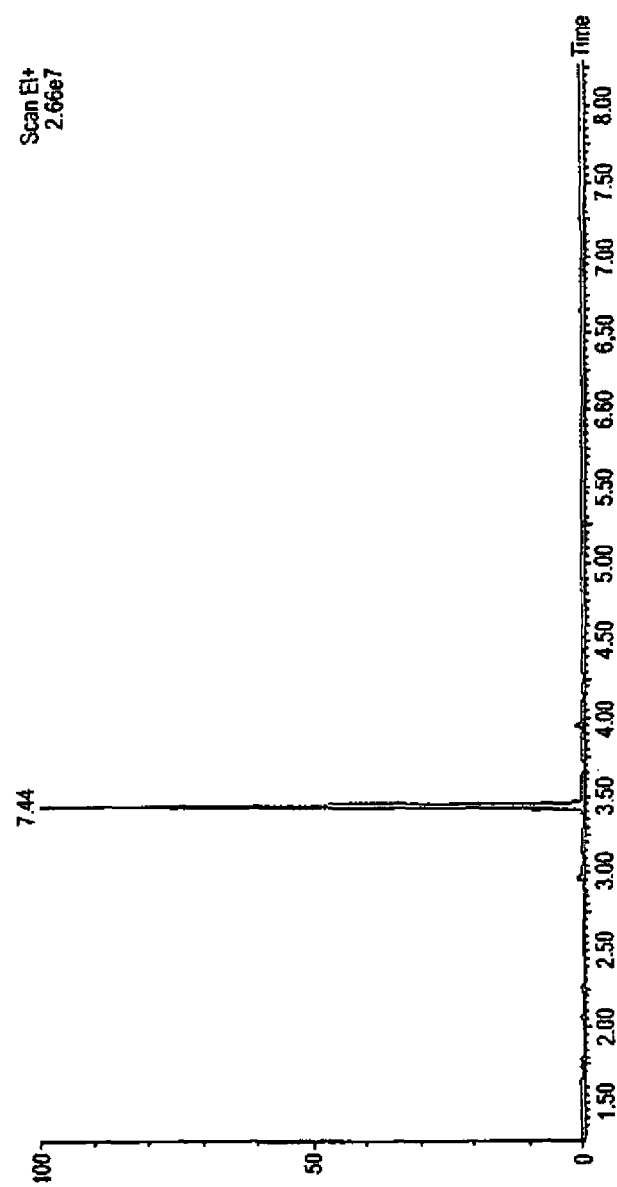
FIG. 10 is total ion current map of the methylated composition KY-1-1.
Figure 11:
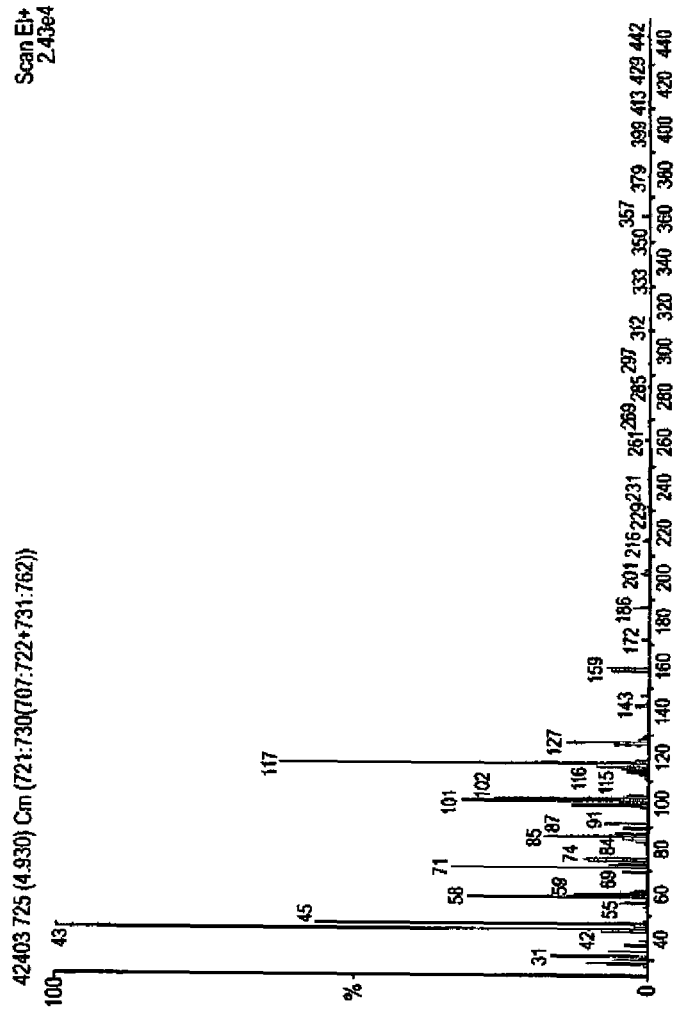
FIG. 11 is a mass spectrum with 3.44 min retention time.

Add 3 ml acetic anhydride into the above product, close the lip, in 100° C. for 1 hour. Add 3 ml toluene, evaporated to dryness. Repeat above 4-5 times. Separate in a separatory funnel with same volume chloroform and water. Remove the upper aqueous phase, and dried by water-free sodium sulfate, shaking 10 minutes, and then remove the sodium sulfate by filtration, evaporated to dryness, and then dissolve in 0.5 ml chloroform, make GC-MS. Referring to FIGS. 10 and 11, the result shows that ion peak 43, 58, 71, 101, 117, 127, 159, 186, 201 in retention time 3.44 min is 1,4-dextran.

(3) Condition of Chromatogram

GC-MS apparatus, equipped with quartz capillary column DB-5MS, 30 m×0.25 mm×0.25 μM. Programmed temperature: initial temperature 80° C. for 1 minute, raise to 200° C. in 5° C./min, and then raise to 215° C. in 2° C./min, then to 270° C. in 20° C./min. Helium as carrier gas. Injection port temperature 250° C., and diversion ratio 1:50. The column flow velocity is 1 ml/min. EI (70 Ev), multiplier 350 v, current of lamp 250 μA, temperature of the interface 200° C., ion source temperature 250° C., scanning range 43-461 amu, and scanning velocity 2.5 scan/s.

6. NMR Analysis of KY-1-1

Dissolve sample of KY-1-1 20 mg into 0.5 ml $D_2O$. Detect it in 500 MHz by a NMR apparatus. $^1$HNMR (25° C. and 60° C.), at 25° C., internal standard is HDO δ4.78. $^{13}$C NMR, external standard is saturated trimethylsilyl propane sulfonate ($D_2O$+DSS) when δ=0.00 ppm. Below 60° C., detect $^1$H—$^1$H COSY ($^1$H—$^1$H correlated spectroscopy), TOCSY (total correlation spectroscopy), HMQC (heteronuclear multiple quantum coherrnce), HMBC (heteronuclear multiple-bond correlation spectroscopy) and NOESY (Overhauser effect spectroscopy).

Figure 12:
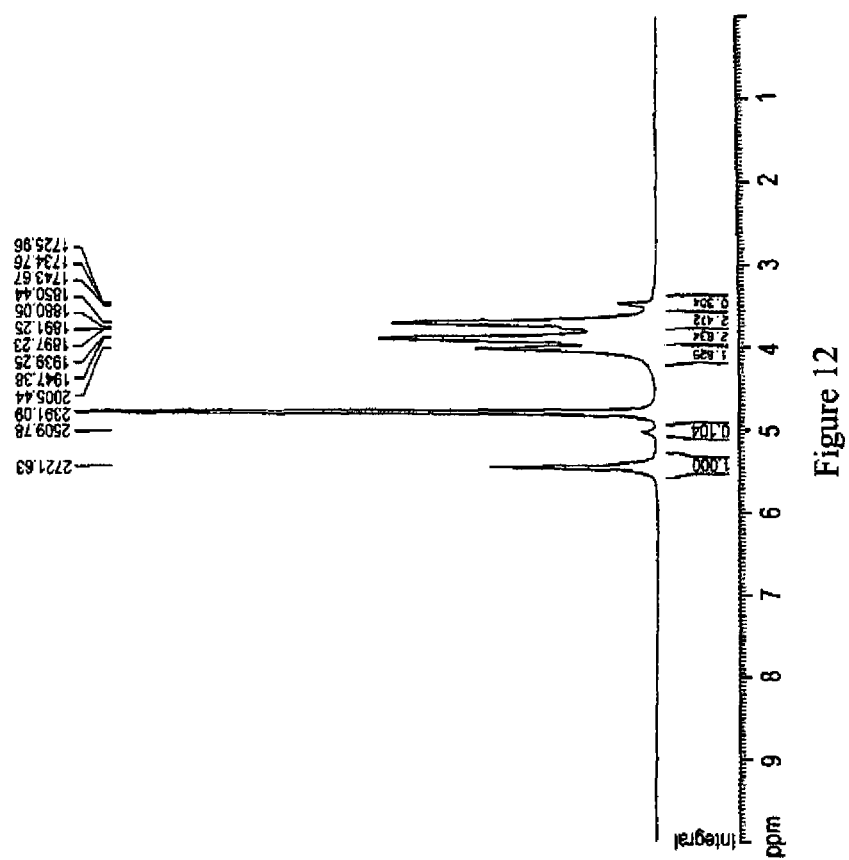
FIG. 12 is a NMR spectra of $^1H$ of the composition KY-1-1 at 27° C.

Referring to FIG. 12, the 27° C. map of $^1$H NMR shows that there is a resonance peak of anomer hydrogen, and there is a small resonance peak at δ 5.02, and there are overlapped resonance peaks at δ 3.50~441.

Figure 13:
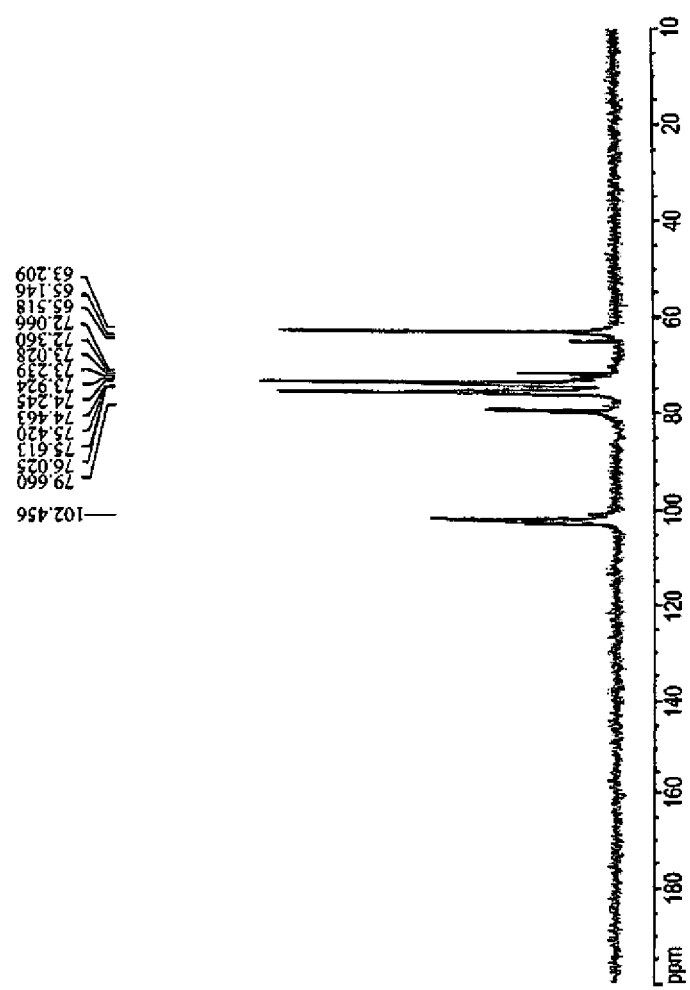
FIG. 13 is a NMR spectra of $^{13}C$ of the composition KY-1-1 at 27° C.
Figure 14:
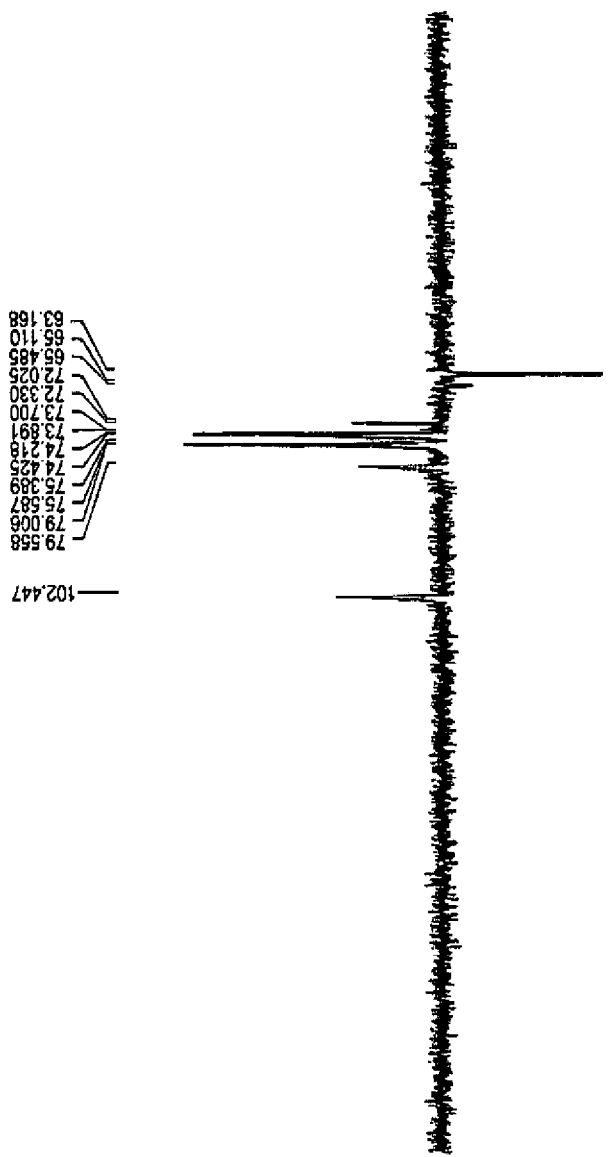
FIG. 14 is a NMR spectra of $^{13}C$ DEPT-135 of the composition KY-1-1 at 27° C.

Referring to FIG. 13, the map of $^{13}$C NMR shows that the region δ 102.47 has an anomer carbon signal, and there is resonance peak of 6th site of glucose at δ 63.21, and there is no reverse peak at δ 69.0 (see FIG. 14). That means the dextran does not have a residue in 6th site of glucose. The signal of O—C of the dextran is shown at δ 63.21~79.56.

Figure 15:
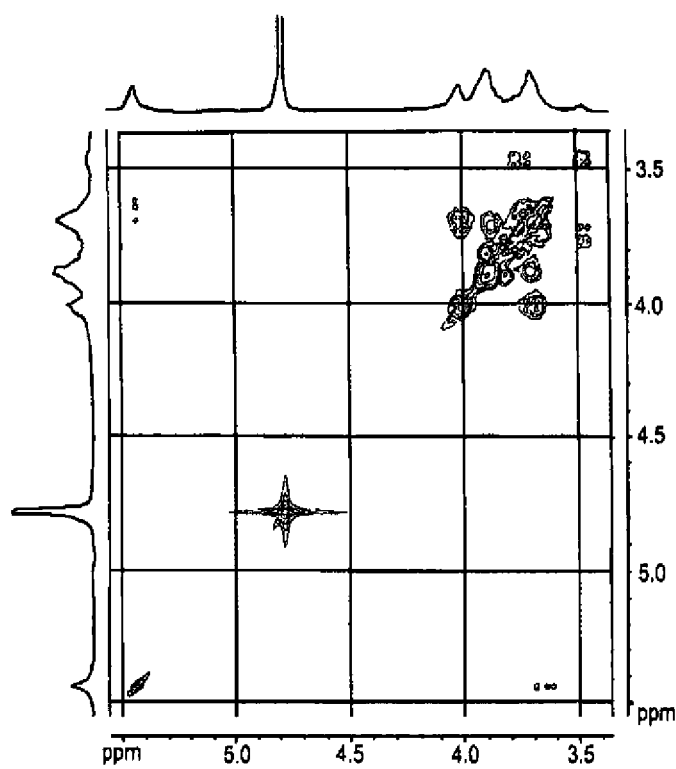
FIG. 15 is a NMR spectra of $^1H$—$^1H$ COSY of the composition KY-1-1.
Figure 16:
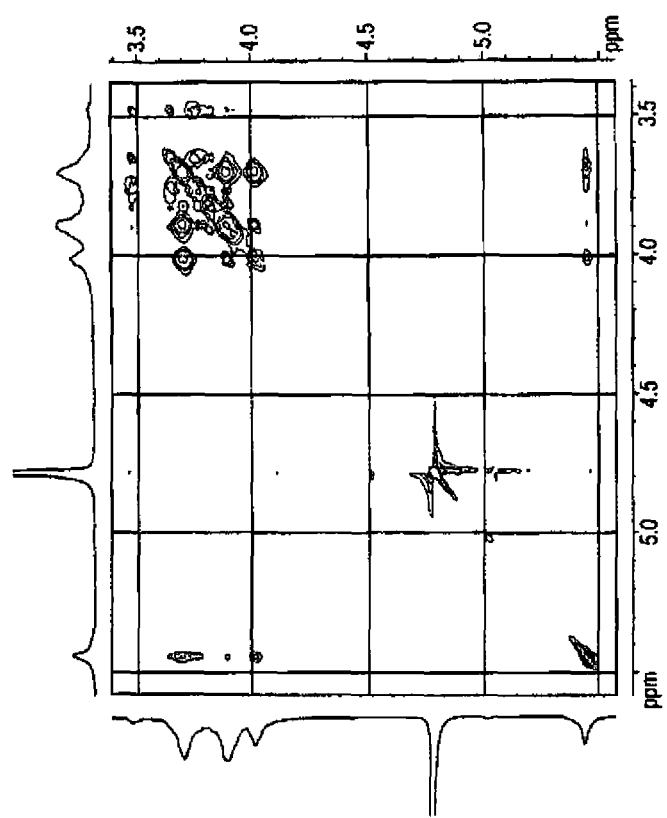
FIG. 16 is a NMR spectra of TOCSY of the composition KY-1-1.
Figure 17:
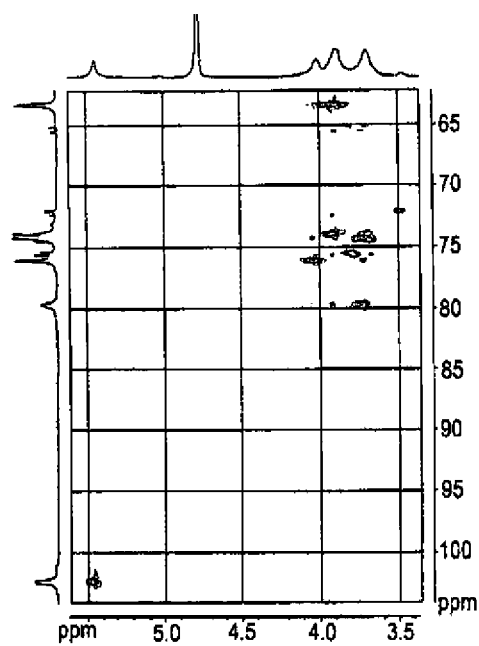
FIG. 17 is a partly NMR spectra of HMQC of the composition KY-1-1.
Figure 18:
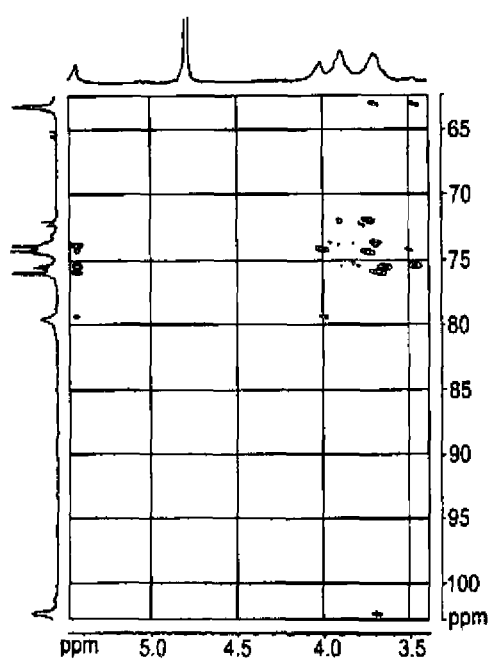
FIG. 18 is a NMR spectra of HMBC of the composition KY-1-1.

$^1$H—$^1$H COSY map (see FIG. 15) and TOCSY map (see FIG. 16) show the chemical shift of the hydrogen. Derivation of the chemical shift of the hydrogen (see Table II) with HMQC map (see FIG. 17).

TABLE II chemical shift of KY-1-1

| Residue of Dextran | | Chemical Shift of H and C | | | | | |
|---|---|---|---|---|---|---|---|
| | | 1 | 2 | 3 | 4 | 5 | 6a | 6b |
| →4)-α-D-Glcp | H | 5.44 | 3.69 | 4.01 | 3.74 | 3.89 | 3.79 | 3.87 |
| | C | 102.45 | 74.42 | 76.01 | 79.56 | 73.89 | 63.17 | |

The chemical shift of residue→4)-α-D-Glcp is more than 5.00 ppm, and there is a single peak in the $^1$H NMR map of H-1, $J_{H-1, H-2}$<3 Hz, and there are overlap peaks in NOESY of H-1/H-2. Above shows that the anomer region has α-configuration. The chemical shift of residue→4)-α-D-Glcp is 7 ppm than the chemical shift of non-substitute monosaccharide residue. That means these sites are substitute sites. The result is correspond with the analysis result of GC-MS.

Figure 19:
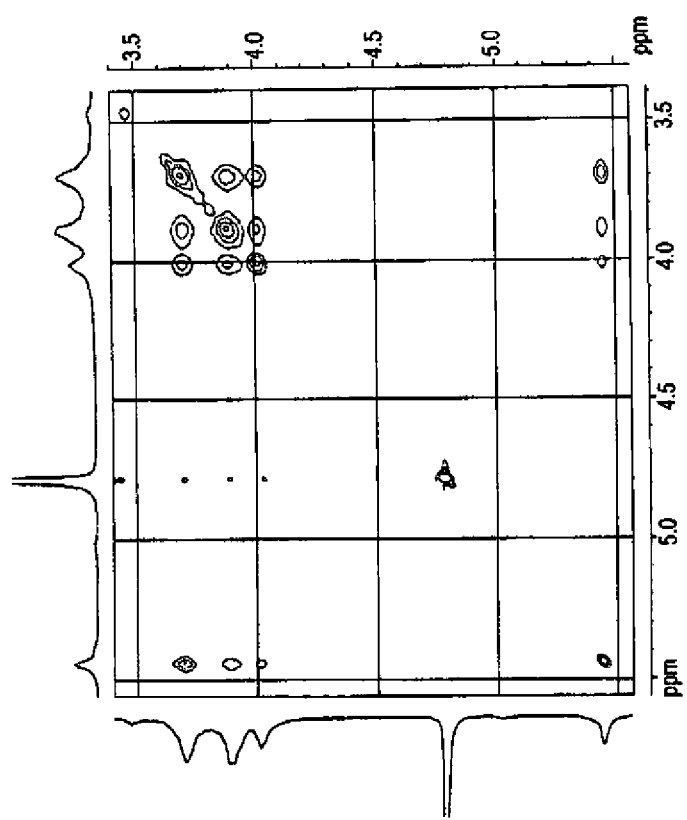
FIG. 19 is a NMR spectra of NOESY of the composition KY-1-1.

HMBC map of residues in repeated structure unit of KY-1-1 shows that there are corresponding peaks for H1 and C4. NOESY may (see FIG. 19) shows that there are corresponding peaks for H1 and H4. These evidences show that the repeated structure unit is α-1,4-dextran.

As a conclusion, KY-1-1 is a dextran in α-configuration, α-1,4-dextran. The dextran comprises the following repeated structure unit:

→4)-α-D-Glcp-(1→4)-α-D-Glcp-(1→

The stereo chemical formula of dextran KY-1-1 is following:

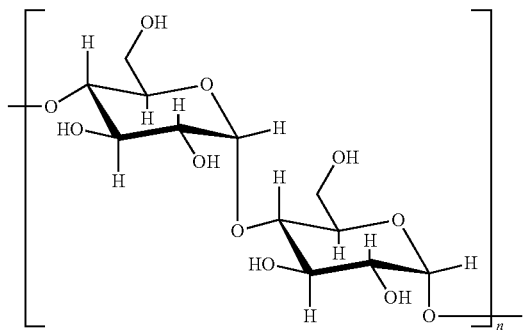

III. Pharmacodynamics Experiment of KY-1-1

1. Material and Method (1) Material

Human lung cancer cell (A549), purchased from cell center of Xiangya School of Medicine, Central South University. Human small cell lung cancer (NCl-H446) and Chinese Hamster Lung Epithelial cells (CHL), purchased from Shanghai Institute of Biochemistry and Cell Biology, Chinese Academy of Sciences. Culture condition: RPMI 1640 medium with 10% bovine serum, 37° C., 5% $CO_2$. Take the logarithmic phase cell for the following experiment.

Weight 3.8 g KY-1-1 into 10 ml bottle, dissolve with DMSO, and then dilute with normal saline (N.S.) to 300.0 μg/ml, 100.0 μg/ml, 30.0 μg/ml, 10.0 μg/ml, 3.0 μg/ml, 1.0 μg/ml, put into 2 ml EP tube separately, preserve in 4° C.

Injection Cisplatin (DDP), purchased from Qilu Pharmaceutical Co., Ltd., 10 mg/bottle, batch number 6030052 DB, dissolve with normal saline, dilute to 100.0 μg/ml, 10.0 μg/ml and 1.0 μg/ml.

Taxol (TAX), purchased from Beijing Sihuan Pharmaceutical Technology Stock Company, 30 mg/5 ml/bottle, batch number 060830, dissolve with normal saline, dilute to 100.0 μg/ml, 10.0 μg/ml and 1.0 μg/ml.

(2) Method

1) Selective Inhibitory Activity to Proliferation of Lung Cancer Cell

Preparing suspension of human lung cancer cell (A549), human small cell lung cancer (NCl-H446) and Chinese Hamster Lung Epithelial cells (CHL), adjust to $0.5 \times 10^4$ cells/ml, seed in 96-microplate, 180 μl/hole. After cell adhesion (about 12 hours), add sample and control solution 20 μl separately into each hole, adjust the final concentration of KY-1-1 to 0.1 μg/ml, 0.3 μg/ml, 1.0 μg/ml, 3.0 μg/ml, 10.0 μg/ml and 30.0 μg/ml, and the final concentration of DDP and TAX are both 0.1 μg/ml, incubate for 48 hours, and then add MTT (5 mg/ml, MTT:PBS) 20 μl to each hole, incubate for 6 hours, remove the liquid in each hole, and then add DMSO 100 μl to each hole in order to dissolve the purple blue precipitate, then detect the absorbency (A) in 570 nm by an enzyme-labeled instrument EXL-800. Calculate the inhibition ratio (IR) with the following equation:

IR(%)=(1−mean of A of dextran group/mean of A of control group)×100%.

The selective index (SI) of cytotoxicity of the dextran is calculated with the following equation:

SI=$IC_{50}$(CHL cells)/$IC_{50}$(A549 cells or NCl-H446 cells), wherein $IC_{50}$ is calculated by Calcus Zn procedure.

Repeat the above experiment twice.

2) KY-1-1's Effect to Anchorage-Dependent Cell Growth Capacity of Lung Cancer

Preparing suspension of human lung cancer cell (A549) and human small cell lung cancer (NCl-H446), adjust to $0.3 \times 10^3$ cells/ml. In each hole, cell suspension 18 ml, and sample 0.2 ml, and control solution 0.2 ml. The final concentration of KY-1-1 is 0.1 µg/ml, 0.3 µg/ml, 1.0 µg/ml, 3.0 µg/ml, 10.0 µg/ml and 30.0 µg/ml, and the final concentration of DDP and TAX are both 0.1 µg/ml, add the same volume medium into the control group. Three holes in each group, seed in 24-microplate, incubate in $CO_2$ for 7 days. Add 95% methanol 0.5 ml into each hole, fixed for 15 minutes, and Giemsa staining for 10-30 minutes. The number of cells in a colony is more than 50, or the diameter of the colony is more than 75 µm. Count the number of colonies in each hole, calculate the mean and record it. Calculate the colony inhibition ratio (CIR) with the following equation:

CIR(%)=(1−mean of number of colony of dextran group/mean of number of colony of control group)×100%.

The plate efficiency (PE) is calculated with the following equation:

PE=mean of number of colony/number of seeded cells×100%, wherein $IC_{50}$ is calculated by Calcus Zn procedure.

Repeat the above experiment twice.

3) KY-1-1's Effect to Anchorage-Independent Cell Growth Capacity of Lung Cancer

Take 24-microplate, add 0.6% agar medium 0.5 ml in each hole. Preparing suspension of human lung cancer cell (A549) and human small cell lung cancer (NCl-H446), adjust to $1.6 \times 10^3$ cells/ml. In each hole, cell suspension 1.6 ml, and sample 0.2 ml, and control solution 0.2 ml. The final concentration of KY-1-1 is 0.1 µg/ml, 0.3 µg/ml, 1.0 µg/ml, 3.0 µg/ml, 10.0 µg/ml and 30.0 µg/ml, and the final concentration of DDP and TAX are both 0.1 µg/ml. DDP 0.2 ml, and TAX 0.2 ml. Add the same volume medium into the control group. Three holes in each group, after mixing with 0.3% agar 0.2 ml, seed in 24-microplate 0.5 ml/hole, incubate in $CO_2$ for 7 days. The number of cells in a colony is more than 50, or the diameter of the colony is more than 75 µm. Count the number of colonies in each hole, calculate the mean and record it. Calculate the colony inhibition ratio (CIR) with the following equation:

CIR(%)=(1−mean of number of colony of dextran group/mean of number of colony of control group)×100%.

The plate efficiency (PE) is calculated with the following equation:

PE=mean of number of colony/number of seeded cells×100%, wherein $IC_{50}$ is calculated by Calcus Zn procedure.

Repeat the above experiment twice.

4) Statistical Methods

Experiment data is expressed by $\bar{X} \pm SD$, and use the software SPSS 15.0 Evaluation for windows to carry out One Way ANOVA analysis, and the analysis of variance uses the LSD method and SNK method. The result is compared by Student's test, there is statistic marked difference under the condition of $p > 0.05$.

2. Steps and Result of Experiments (1) KY-1-1's Effect to Cell Proliferation of Chinese Hamster Lung Epithelial Cells (CHL)

As shown in table III, there is no inhabitation effect for KY-1-1 to the cell proliferation of Chinese Hamster Lung Epithelial cells (CHL). Its $IC_{50}$ value is 411.98 µg/ml.

TABLE III

KY-1-1's effect to cell proliferation of Chinese Hamster Lung Epithelial cells (CHL) (n = 9, $\bar{X} \pm SD$)

| Group | Concentration (µg/ml) | A570 | IR (%) | $IC_{50}$ (µg/ml) |
|---|---|---|---|---|
| Control | N.S. | 1.84 ± 0.06 | — | — |
| Menstruum | 0.02% DMSO | 1.82 ± 0.04 | 3.41 | — |
| TAX | 0.1 | 1.25 ± 0.14** | 83.13 | — |
| DDP | 0.1 | 1.41 ± 0.30** | 76.35 | — |
| KY-1-1 | 0.1 | 1.80 ± 0.05** | 7.25 | 411.98 |
| KY-1-1 | 0.3 | 1.73 ± 0.01* | 16.87 | — |
| KY-1-1 | 1.0 | 1.65 ± 0.02** | 25.45 | — |
| KY-1-1 | 3.0 | 1.53 ± 0.01** | 35.96 | — |
| KY-1-1 | 10.0 | 1.52 ± 0.01** | 49.08 | — |
| KY-1-1 | 30.0 | 1.48 ± 0.03** | 63.89 | — |

*$P < 0.05$ vs. Control;
**$P < 0.01$ vs. Control.

(1) KY-1-1's Effect to Cell Proliferation of Human Small Cell Lung Cancer (NCl-H446)

As shown in table IV, there is remarkable inhabitation effect for KY-1-1 to the proliferation of human small cell lung cancer (NCl-H446), and the effect is depend on the dose of KY-1-1. Its $IC_{50}$ value is 7.22 µg/ml. It is proved that KY-1-1 has selective inhibitory activity to the cell proliferation of human small cell lung cancer (NCl-H446), and has low cytotoxicity. The selective index of cytotoxicity of KY-1-1 to human small cell lung cancer (NCl-H446) is 57.06 (411.98/7.22).

TABLE IV

KY-1-1's effect to cell proliferation of human small cell lung cancer (NCI-H446) (n = 9, $\bar{X} \pm SD$)

| Group | Concentration (µg/ml) | A570 | IR (%) | $IC_{50}$ (µg/ml) |
|---|---|---|---|---|
| Control | N.S. | 1.63 ± 0.10 | — | — |
| Menstruum | 0.02% DMSO | 1.59 ± 0.10 | 2.27 | — |
| TAX | 0.1 | 0.27 ± 0.01** | 83.54 | — |
| DDP | 0.1 | 0.36 ± 0.03** | 77.89 | — |
| KY-1-1 | 0.1 | 1.58 ± 0.11 | 2.55 | 7.22 |
| KY-1-1 | 0.3 | 1.33 ± 0.05** | 18.20 | — |
| KY-1-1 | 1.0 | 1.16 ± 0.06** | 28.54 | — |
| KY-1-1 | 3.0 | 1.01 ± 0.07** | 38.12 | — |
| KY-1-1 | 10.0 | 0.80 ± 0.04** | 50.98 | — |
| KY-1-1 | 30.0 | 0.52 ± 0.02** | 67.94 | — |

**$P < 0.01$ vs. Control.

(3) KY-1-1's Effect to Cell Proliferation of Human Lung Cancer (A549)

As shown in table V, there is remarkable inhabitation effect for KY-1-1 to the cell proliferation of human lung cancer (A549), and the effect is depend on the dose of KY-1-1. Its $IC_{50}$ value is 9.44 µg/ml. It is proved that KY-1-1 has selective inhibitory activity to the cell proliferation of human lung cancer (A549), and has low cytotoxicity. The selective index of cytotoxicity of KY-1-1 to human lung cancer (A549) is 43.64 (411.98/9.44).

TABLE V

KY-1-1's effect to cell proliferation of human lung cancer
(A549) (n = 9, $\overline{X} \pm SD$)

| Group | Concentration (µg/ml) | A570 | IR (%) | IC$_{50}$ (µg/ml) |
|---|---|---|---|---|
| Control | N.S. | 1.57 ± 0.09 | — | — |
| Menstruum | 0.02% DMSO | 1.52 ± 0.10 | 3.41 | — |
| TAX | 0.1 | 0.27 ± 0.03** | 83.13 | — |
| DDP | 0.1 | 0.37 ± 0.03** | 76.35 | — |
| KY-1-1 | 0.1 | 1.46 ± 0.07** | 7.25 | 9.44 |
| KY-1-1 | 0.3 | 1.31 ± 0.12** | 16.87 | — |
| KY-1-1 | 1.0 | 1.17 ± 0.11** | 25.45 | — |
| KY-1-1 | 3.0 | 1.01 ± 0.08** | 35.96 | — |
| KY-1-1 | 10.0 | 0.80 ± 0.03** | 49.08 | — |
| KY-1-1 | 30.0 | 0.57 ± 0.05** | 63.89 | — |

**P < 0.01 vs. Control.

(4) KY-1-1's Effect to Anchorage-Dependent Cell Growth Capacity of Human Small Cell Lung Cancer (NCl-H446)

As shown in table VI, there is remarkable inhabitation effect for KY-1-1 to the anchorage-dependent cell growth capacity of human small cell lung cancer (NCl-H446), and the effect is depend on the dose of KY-1-1. Its IC$_{50}$ value is 7.01 µg/ml.

TABLE VI

KY-1-1's effect to anchorage-dependent cell growth capacity of human
small cell lung cancer (NCl-H446), detected by plate
cloning method (n = 9, $\overline{X} \pm SD$)

| Group | Concentration (µg/ml) | Number of Colonies | IR (%) | IC$_{50}$ (µg/ml) |
|---|---|---|---|---|
| Control | N.S. | 108.22 ± 4.79 | — | — |
| Menstruum | 0.02% DMSO | 105.78 ± 5.09 | 2.26 | — |
| TAX | 0.1 | 19.11 ± 2.57** | 82.34 | — |
| DDP | 0.1 | 23.33 ± 4.18** | 78.44 | — |
| KY-1-1 | 0.1 | 106.56 ± 6.95 | 1.54 | 7.01 |
| KY-1-1 | 0.3 | 89.11 ± 2.76** | 17.66 | — |
| KY-1-1 | 1.0 | 76.89 ± 5.28** | 28.95 | — |
| KY-1-1 | 3.0 | 63.78 ± 3.31** | 41.07 | — |
| KY-1-1 | 10.0 | 49.78 ± 3.38** | 54.00 | — |
| KY-1-1 | 30.0 | 37.67 ± 3.28** | 65.19 | — |

**P < 0.01 vs. Control.

(5) KY-1-1's Effect to Anchorage-Dependent Cell Growth Capacity of Human Lung Cancer (A549)

As shown in table VII, there is remarkable inhabitation effect for KY-1-1 to the anchorage-dependent cell growth capacity of human lung cancer (A549), and the effect is depend on the dose of KY-1-1. Its IC$_{50}$ value is 8.94 µg/ml.

TABLE VII

KY-1-1's effect to anchorage-dependent cell growth capacity of
human lung cancer (A549), detected by plate cloning
method (n = 9, $\overline{X} \pm SD$)

| Group | Concentration (µg/ml) | Number of Colonies | IR (%) | IC$_{50}$ (µg/ml) |
|---|---|---|---|---|
| Control | N.S. | 98.78 ± 5.21 | — | — |
| Menstruum | 0.02% DMSO | 96.11 ± 3.95 | 2.70 | — |
| TAX | 0.1 | 17.78 ± 2.05** | 82.00 | — |
| DDP | 0.1 | 23.89 ± 4.43** | 75.82 | — |
| KY-1-1 | 0.1 | 95.56 ± 4.88 | 3.26 | 8.94 |
| KY-1-1 | 0.3 | 78.67 ± 4.00** | 20.36 | — |
| KY-1-1 | 1.0 | 72.22 ± 3.53** | 26.88 | — |
| KY-1-1 | 3.0 | 63.78 ± 3.31** | 35.43 | — |
| KY-1-1 | 10.0 | 51.11 ± 2.32** | 48.26 | — |
| KY-1-1 | 30.0 | 36.11 ± 6.33** | 63.44 | — |

**P < 0.01 vs. Control.

(6) KY-1-1's Effect to Anchorage-Independent Cell Growth Capacity of Human Small Cell Lung Cancer (NCl-H446)

As shown in table VIII, there is remarkable inhabitation effect for KY-1-1 to the cell colony forming capacity of human small cell lung cancer (NCl-H446), and the effect is depend on the dose of KY-1-1. Its IC$_{50}$ value is 7.60 µg/ml.

TABLE VIII

KY-1-1's effect to cell colony forming capacity of human small cell
lung cancer (NCl-H446) (n = 9, $\overline{X} \pm SD$)

| Group | Concentration (µg/ml) | Number of Colonies | IR (%) | IC$_{50}$ (µg/ml) |
|---|---|---|---|---|
| Control | N.S. | 70.78 ± 3.38 | — | — |
| Menstruum | 0.02% DMSO | 68.78 ± 3.96 | 2.83 | — |
| TAX | 0.1 | 11.00 ± 1.58** | 84.46 | — |
| DDP | 0.1 | 17.00 ± 2.74** | 75.98 | — |
| KY-1-1 | 0.1 | 68.22 ± 1.99 | 3.61 | 7.60 |
| KY-1-1 | 0.3 | 59.33 ± 2.65** | 16.17 | — |
| KY-1-1 | 1.0 | 49.78 ± 1.86** | 29.67 | — |
| KY-1-1 | 3.0 | 43.22 ± 3.73** | 38.93 | — |
| KY-1-1 | 10.0 | 34.44 ± 2.51** | 51.33 | — |
| KY-1-1 | 30.0 | 24.44 ± 2.51** | 65.46 | — |

**P < 0.01 vs. Control.

(7) KY-1-1's Effect to Anchorage-Independent Cell Growth Capacity of Human Lung Cancer (A549)

As shown in table IX, there is remarkable inhabitation effect for KY-1-1 to the cell colony forming capacity of human lung cancer (A549), and the effect is depend on the dose of KY-1-1. Its IC$_{50}$ value is 9.11 µg/ml.

TABLE IX

KY-1-1's effect to cell colony forming capacity of human lung cancer
(A549) (n = 9, $\overline{X} \pm SD$)

| Group | Concentration (µg/ml) | Number of Colonies | IR (%) | IC$_{50}$(µg/ml) |
|---|---|---|---|---|
| Control | N.S. | 61.00 ± 2.74 | — | — |
| Menstruum | 0.02% DMSO | 58.89 ± 3.44 | 3.46 | — |
| TAX | 0.1 | 10.00 ± 1.87** | 83.61 | — |
| DDP | 0.1 | 14.00 ± 2.00** | 77.05 | — |
| KY-1-1 | 0.1 | 57.44 ± 3.64* | 5.83 | 9.11 |
| KY-1-1 | 0.3 | 51.22 ± 4.82** | 16.03 | — |
| KY-1-1 | 1.0 | 44.33 ± 3.46** | 27.32 | — |
| KY-1-1 | 3.0 | 39.22 ± 2.11** | 35.70 | — |
| KY-1-1 | 10.0 | 29.78 ± 2.33** | 51.18 | — |
| KY-1-1 | 30.0 | 22.89 ± 2.62** | 62.48 | — |

*P < 0.05 vs. Control;
**P < 0.01 vs. Control.

IV. Anti-Lung Cancer Pharmaceutical Composition Comprising of the Dextran

1. Frozen Powder for Injection of the Dextran

Preparing the frozen powder for injection as following:

Take KY-1-1 10 g, Mannitol 1000 g (excipient), add water for injection to 1000 ml and mix them, adjust to pH 5.0-5.5, add 0.05% activated carbon at 40-45° C. for 15 minutes, first filtered by 0.45 µm micro-membrane, and then filtered by 0.22 µm micro-membrane to clear, and then detect the content and pH, separate the product into bottles for injection, 5 ml/bottle. Freeze drying, packaging, and sterilization. Obtain 100 mg/bottle.

Dosage and Administration:

Take the dextran 100 mg, add 5% glucose solution, intravenous drip for 30 minutes. Twice one day, and one course of medical treatments is 21 days. Several courses would be used depended on the condition of the patient.

2. Injection of the Dextran

Preparing the frozen powder for injection as following:

Take KY-1-1 10 g, Mannitol 1000 g (excipient), add water for injection to 1000 ml and mix them, adjust to pH 5.0-5.5, add 0.05% activated carbon at 40-45° C. for 15 minutes, first filtered by 0.45 μm micro-membrane, and then filtered by 0.22 μm micro-membrane to clear, and then detect the content and pH, separate the product into 5 ml ampoules. Packaging, and sterilization. Obtain 100 mg/ampoule (5 ml ampoule).

Dosage and Administration:

Take the dextran 100 mg (100 mg/ampoule), add 5% glucose solution, intravenous injection.

In other embodiments of the present invention, the pharmaceutical composition comprises of effective amount of the dextran, and pharmaceutically acceptable excipients, thinners, and carriers. The pharmaceutical composition is in the form of: capsule, granulate, tablet, pill, and guttate pill.

It will be appreciated that the above descriptions are intended only to serve as examples, and that many other embodiments are possible within the scope of the present invention as defined in the appended claims.

The invention claimed is:

1. A method of preparing a pharmaceutical composition of an isolated polymer, extracted from Limax, with molecular weight of 1.5-2.5 million daltons for treatment of lung cancer, comprising the steps of:

mixing the polymer mixing the polymer of glucose with Mannitol and water to form a composition; adjusting acidity level of the composition to pH 5; adding an activated carbon to the composition at 40-45° C. for 15 minutes; and filtering the composition by a micro-membrane, wherein the polymer of glucose comprises 1:4 glucoside linkage having a repeated chemical structure unit of: →4)-α-D-Glcp-(1→4)-α-D-Glcp-(1→, and a stereo chemical formula of:

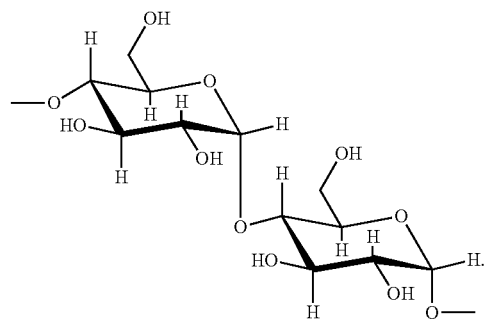

* * * * *